United States Patent [19]
Samson et al.

[11] Patent Number: 5,766,160
[45] Date of Patent: Jun. 16, 1998

[54] VARIABLE STIFFNESS COILS

[75] Inventors: Gene Samson, Milpitas; Ivan Sepetka, Los Altos; U. Hiram Chee, San Carlos; Christopher G. M. Ken, San Mateo; Nga T. Van, Santa Clara, all of Calif.

[73] Assignee: Target Therapeutics, Inc., Fremont, Calif.

[21] Appl. No.: 480,042

[22] Filed: Jun. 6, 1995

[51] Int. Cl.⁶ .................................. A61B 17/00
[52] U.S. Cl. .............................. 606/1; 606/108
[58] Field of Search .................. 606/1, 108, 151, 606/190–200; 623/1, 11, 12

[56] References Cited

U.S. PATENT DOCUMENTS

| | | |
|---|---|---|
| 485,652 | 11/1892 | Pfingst . |
| 4,553,545 | 11/1985 | Maass et al. . |
| 4,760,849 | 8/1988 | Kropf . |
| 4,830,023 | 5/1989 | de Toledo et al. . |
| 4,994,069 | 2/1991 | Ritchart et al. ............... 606/191 |
| 5,069,217 | 12/1991 | Fleischhaker, Jr. . |
| 5,171,383 | 12/1992 | Sagaye et al. . |
| 5,354,295 | 10/1994 | Guglielni et al. ............. 606/108 |
| 5,382,259 | 1/1995 | Phelps et al. . |
| 5,476,472 | 12/1995 | Dormandy et al. ............ 606/108 |

*Primary Examiner*—Glenn K. Dawson
*Attorney, Agent, or Firm*—Morrison & Foerster LLP

[57] ABSTRACT

This invention is an implantable vaso-occlusive device. It is a helically wound coil having a central section along its longitudinal axis which is somewhat stiffer than at least one of its end regions.

14 Claims, 3 Drawing Sheets

VARIABLE STIFFNESS COILS

FIELD OF THE INVENTION

This invention is an implantable vaso-occlusive device. It is a helically wound coil having a central section along its longitudinal axis which central section is somewhat stiffer than at least one of its end regions.

BACKGROUND OF THE INVENTION

Many commercially available vaso-occlusive coils have capped ends which are formed by the simple procedure of heating the coil end sufficiently to liquify the composite metal into a round cap-like artifice. Although the rounded cap provides a surface which is relatively minimal when contacting the internal surface of a delivery catheter, we believe that the tip could be improved upon, at least from the aspect of coil delivery.

Some coils appear to have lost a measure of flexibility in the region near the tip, perhaps because of the heat necessary to melt the metal at the adjoining tip. This short region of stiffness produces a leg which presses against the lumen of the catheter, at least until the tip clears the distal end of that catheter. The energy stored in pushing the coil through the distal end of the catheter causes the coil to jump forward and the catheter to retract as the coil leaves the catheter. If a very precise placement of the catheter tip is desired, e.g., where a small-necked aneurysm is accessed, such a lurching and slipping is particularly not desirable.

Our intent in this invention is to improve the stiffness characteristics of the vaso-occlusive coil so to enhance the ease with which the coils advance through the catheter, improve the handling of the coil as it exits the catheter, and improve the coil's ability to be deployed gently as it leaves the catheter.

Finally, the flexible tip promotes the position stability of the coil during placement. The "droop" of the flexible distal section tends to engage the vessel wall and press the trailing stiffer section of the coil against the opposing wall. The resulting coil mass is formed more quickly and more compactly.

Our solution to this problem is to assure that at least one end of the vaso-occlusive coil is somewhat more flexible than the adjoining midsection. The leading end of the coil, i.e., the end of the coil which is distally placed, is most important, although for practicality's sake, it is desirable that both ends be so constructed. In such a way, the coil may be introduced from the catheter in either direction into the blood system. There are several ways to increase the flexibility of these end regions: vary the diameter of the wire making up the coil, change the spacing of the coil turns, vary the diameter of the coil, and change the inherent properties of the material in the wire, such as by annealing.

This technique is useful whether using coils which have electrolytic or mechanical detachment links at their ends, or when using coils having attached thrombogenic fibers. The technique is especially useful on coils having secondary shapes when those coils are relaxed. There are other helical coil devices having varying pitch spacing or the like.

For instance, U.S. Pat. No. 485,652, to Pfingst, issued Nov. 8, 1892 describes a car spring—apparently a railroad car spring—in which the diameter of the rod making up the coil gradually tapers. The inner diameter of the spring appears to be of constant diameter throughout. It is obviously quite stiff.

U.S. Pat. No. 4,553,545, to Mass et al., shows a intravascular prothesis made up of a helical spring having a variable pitch. The device is intended to hold a human body lumen open and consequently is fairly stiff.

U.S. Pat. No. 4,760,8249 shows a planar blank intended for the manufacture of a coil spring. The coil spring is suitable for a translumenal implantation. The device is either used as a stent to hold a vascular lumen open or it may be used as a blood filter. The coil spring filter may be used as a vena cava inferior filter to prevent the formation of emboli and their passage into the lung.

U.S. Pat. No. 4,830,023, to de Toledo, shows a medical guidewire having a coil tip. The device has a degree of flexibility and a tip region of greater flexibility. The coil making up the helically wound spring is in two pieces: one having a greater pitch than the other.

Similarly, U.S. Pat. No. 5,069,217, to Fleischacker Jr., shows a coil of varying pitch soldered to the end of a guidewire combination.

U.S. Pat. No. 5,171,383, to Segae et al. shows a guidewire having varying flexibility along the axis. The flexibility is varied by changing the heat treatment temperature along the length of the guidewire.

None of these publications show the concept described herein in which at least a portion of the center of the vaso-occlusive device is less flexible than at least one of the ends.

SUMMARY OF THE INVENTION

This invention is an implantable vaso-occlusive device. In general, it is a vaso-occlusive coil which, viewed along its longitudinal axis, has a center section which is somewhat stiffer than one or the other or both of its end sections. This permits the vaso-occlusive device to be deployed more gently from the catheter and results in a procedure which places the coil with more certainty at a specific point in a human body vascular lumen or other site to be occluded.

The device is typically used in the human vasculature to form emboli but may be used in any site in the human body where an occlusion such as one produced by the inventive device is needed.

The device may be made in a number of ways. The wire forming the end section or sections of the vaso-occlusive device may be of a smaller diameter. The wire may be of different physical characteristics. Such differences in physical characteristics may be produced by annealing the wire. The end section or sections may be made more flexible by changing the diameter of the section as compared to the diameter in mid-section.

The device may be used with or without the presence of ancillary fibers (e.g., Dacron) to enhance the device's overall thrombogenicity. The device is preferably made in such a way that it has both a primary coil diameter and, once it is deployed from the catheter, a self-forming secondary form.

DESCRIPTION OF THE INVENTION

This invention is a helically wound vaso-occlusive coil which may be introduced into the human body, particularly into the human vasculature, using a catheter. The inventive coil has at least one region adjacent the end of the coil which has a greater flexibility than the midsection of the coil.

Figure 1:
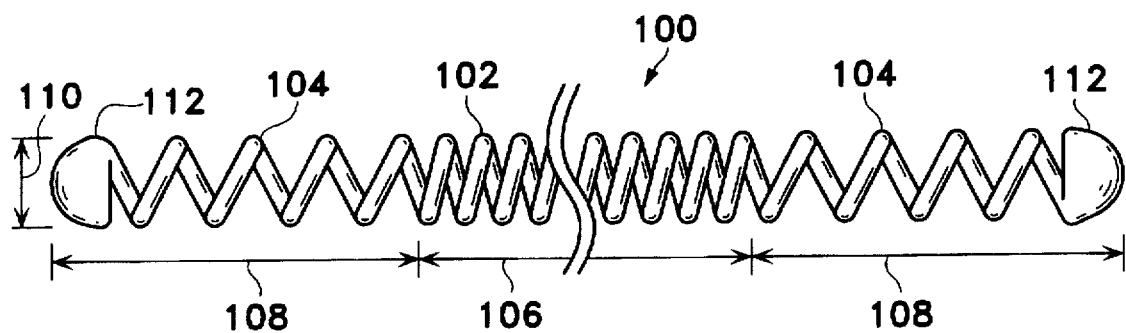
FIG. 1 shows a side view of a generic linear coil for the purpose of depicting the conventions used in describing the inventive device.
Figure 2:
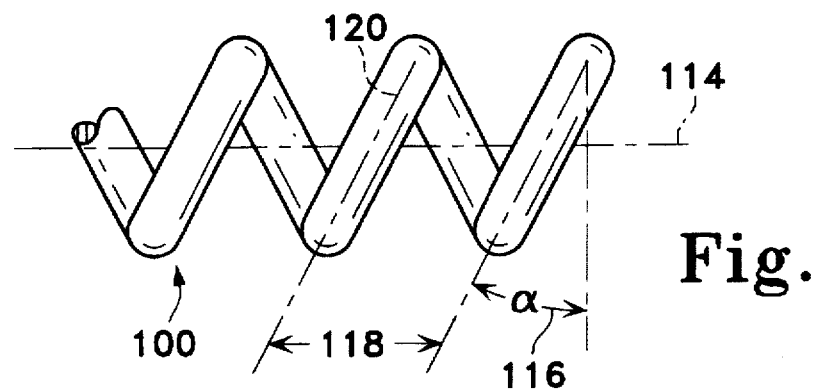
FIG. 2 is a close up of a section of a generally linear coil also for the purpose of depicting the conventions used in describing the inventive device.
Figure 3:
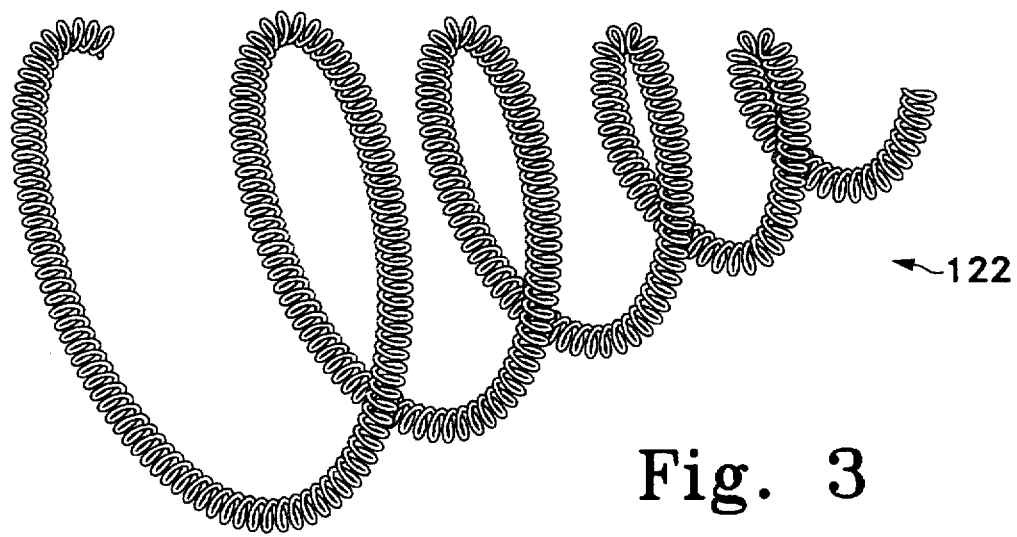
FIG. 3 shows a side view of a device for the purpose of showing a secondary shape.

FIGS. 1-3 show a generally linear coil (100) used to describe the conventions and terms used in relation to this invention. The coil (100) depicted here is made up of a central region (102) and two end regions (104). Central or mid-region (102) has a length (106) and end regions (104) similarly have lengths (108). Although the two lengths of the end regions (104) are shown to be equal to each other, the lengths need not be equal. The coil (100) is helically wound from a wire. The diameter of the coil (100) is referred to as the "primary" diameter (110). The tips or caps (112) are shown at the physical ends of the coils. The tips can be mechanically or electrolytically detachable from a pusher during implantation.

FIG. 2 shows a close-up of a section of a coil (100). FIG. 2 shows the axis (114) of the coil (100). The pitch angle α is shown as (116). That angle is measured from the center of a line (120) of a coil turn to a line perpendicular to the axis (116). As was mentioned above, the pitch spacing or angle may be varied in some aspects of this invention to produce a region of higher flexibility.

Finally, FIG. 3 shows a vaso-occlusive device (122) made according to this invention having what we term a "secondary shape". In this instance the secondary shape is a vortex-like shape. We term the shape "secondary" because it generically is formed by taking a wire which has been formed into a "primary" helical shape (as seen in FIGS. 1 and 2 as (100)) and further forming another shape which is not linear. There are numerous secondary vaso-occlusive coil forms known in the art. A selection of secondary shapes may be found in U.S. Pat. Nos. 4,994,069 (to Ritchart et al.), 5,382,259 (to Phelps et al.), and in 5,304,194 (to Chee); the entirety of which are incorporated by a notice. Specific secondary shapes are not critical to this invention. In many instances of use, it is not critical that the vaso-occlusive device even have a secondary shape. Nevertheless, for many procedures, particularly those involving occlusion of a flowing vascular stream, a secondary shape helps to assure effective embolization. The wire making up the vascular device will typically be of a metallic material, such as platinum, gold, rhodium, rhenium, palladium, tungsten, and the like, as well as alloys of these metals. These metals have significant radiopacity and in their alloys may be tailored to accomplish an appropriate blend of flexibility and stiffness. They are also largely biologically inert. A highly desired metallic composition is a platinum alloy containing a minor amount of tungsten.

The wire may, of course, be of other suitable biocompatible materials, e.g., polymers, composites of metals or alloys and polymers, etc. Polymeric wire materials are often mixed with a radiopaque material, e.g., barium sulfate, bismuth trioxide, bismuth carbonate, powdered tungsten, powdered tantalum, or the like, to promote their passive ability to be visualized during fluoroscopy.

The diameter of the wire often used in this invention will be in the range of 0.0005 and 0.005 inches. Larger diameter wire may be desirable for certain very specific indications where occlusion is needed at a high volume flow rate site. Such might include repair an infant's Vein of Galen and treatment of arteriovenous malformations (AVM's). Larger diameter wire would be chosen because of its springiness. Materials with higher innate springiness, e.g., platinum alloys with high tungsten content, would also be suitable.

The primary coil diameter (110 in FIG. 1) will nominally be in the range of 0.008 to 0.025 inches. For most neurovascular indications, a range of 0.015 to 0.018 inches is preferred. The axial length of the primary shape will usually fall in the range of 0.5 to 100 cm, more usually 2 to 40 cm. Depending upon usage, the coil may well have 10-75 turns per centimeter, preferably 10-40 turns per centimeter. All of the dimensions here are provided only as guidelines and are not critical to the invention. However, only dimensions suitable for use in occluding sites within the human body are included in the scope of this invention.

Figure 4:
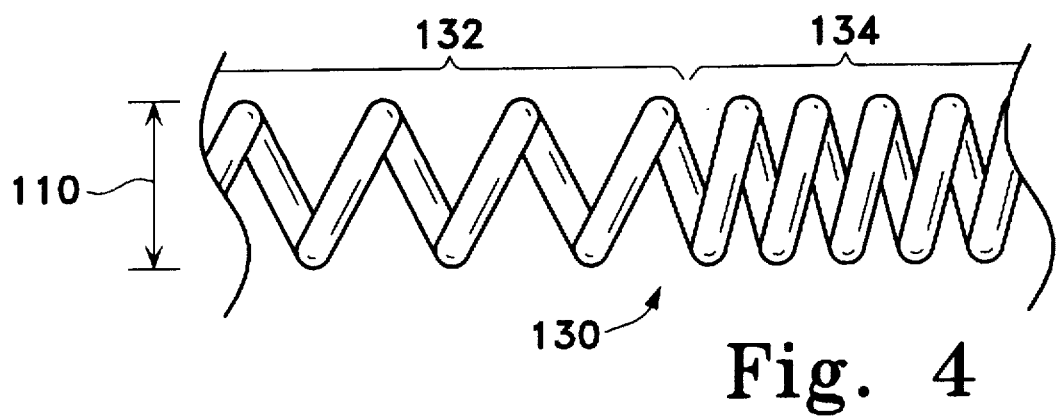
FIG. 4 shows a partial side view of the device made according to the invention in which the spacing of helical turns of the coil is varied.

FIG. 4 shows one variation of the inventive vaso-occlusive device. A magnified, partial side view of a coil (130) is seen. In this view, the diameter of the wire and the primary diameter (110) of the coil is maintained to be approximately or substantially constant in the end region (132) and in the center region (134). We say "approximately or substantially constant" in that one excellent way to produce the coils of this invention involves winding the coil stock at nominally constant pitch and simply stretching one or more of the ends to produce the increased pitch spacing. The diameter of the coil in the stretched region will obviously decrease when such a step is taken.

For the coil wire diameters, wire compositions, and pitch spacings with which we are familiar, an increased pitch spacing of 25% or more is sufficient to provide the increased lateral flexibility to attain the goals of the invention. The length of the end regions (e.g., (104) in FIG. 1 and (132) in FIG. 4; others discussed below) may be selected in several ways. For instance, for most coils, an end region in length of at least 1.5 times the diameter of the selected vascular region is sufficient. This may translate into an end region length of 2-3 mm in some cases. A length of 0.5 to 1.5 cm is typical. The total percentage of comparative high flexibility would typically lie between 2.5 and 20% of the total primary axial length of the coil.

The flexibility of this variation of the coil and its brethren discussed below are all measured perpendicular to the coil axis using a "rolling" 1-cm moment arm. That is to say that a specific coil is grasped at a point and the force is applied one centimeter away. The force required to achieve a specific deflection for the coil in the more flexible end section is compared to the less flexible mid-section. The ratio of these forces (i.e., force per unit deflection in end section:: force per unit deflection in mid-section) should be less than 1.0. Typically the ratio will be between 0.35 and 0.95 with a preferred range of 0.4 to 0.75, most preferably 0.6 to 0.75.

Figure 5:
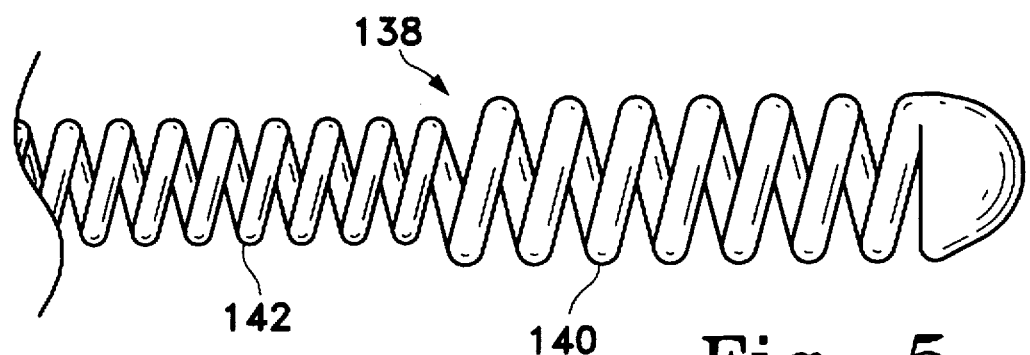
FIG. 5 shows a side view of a variation of the inventive device in which the diameter of the helical coil is varied to provide differences in flexibility.

FIG. 5 shows a further variation of the invention in which the enhanced flexibility of the end portion is provided by a variation in the primary diameter of the vaso-occlusive coil.

FIG. 5 shows the portion of a coil (138) having an end section (140) and a primary diameter somewhat larger than the primary diameter of the mid-section (142). The diameter of end section (140) is sufficiently larger than the diameter of mid-section (142) so that it is able to meet the criteria mentioned above. That is to say that the ratio of force needed for a unit deflection of the end section is less than the unit of force needed to deflect an isolated portion of the mid-section (142); and preferably is of a ratio between 0.5 and 0.95.

Figure 6:
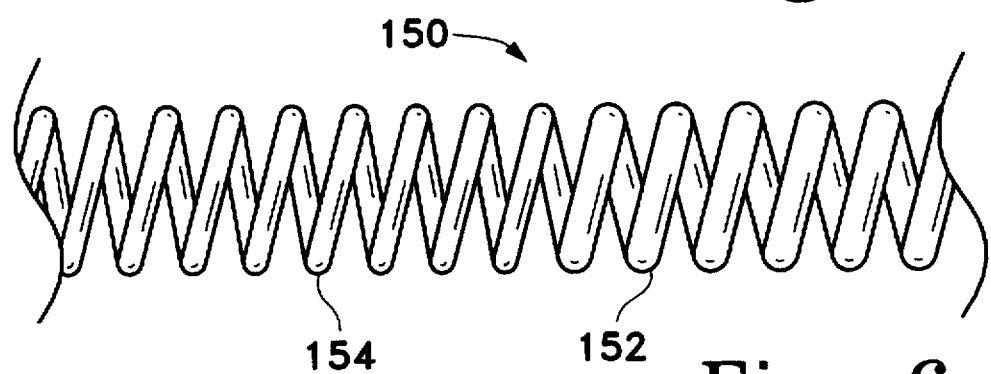
FIG. 6 shows a variation of the invention in which the diameter of the wire is varied in order to vary the resulting flexibility of the inventive vaso-occlusive device.

FIG. 6 shows another variation of the inventive vaso-occlusive helical coil (150) in which the diameter of the wire making up mid-section (152) is larger than the diameter of the wire making up at least one end section (154). This axially contiguous relationship between two sections of the coil may be carried out by providing the coil wire to the device for rolling the primary coil in a series of different diameters. The two sections may be brazed or soldered together. Again, it is only necessary that the two sections (152) be of different wire diameters, and hence flexible, to conform to this variation of the invention. As is the case with all of these variations, the variation desirably has a secondary shape such as one of those mentioned above.

Figure 7:
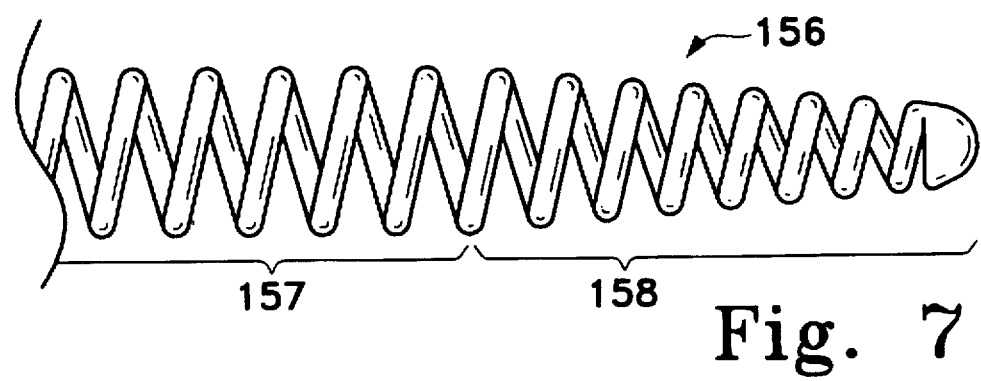
FIG. 7 shows a variation of the invention in which the diameter of the end section of the coil is varied in order to vary the resulting flexibility of the inventive vaso-occlusive device.

FIG. 7 shows a variation of the inventive device in which the flexibility of the end section is varied throughout the end section. The concept behind this variation may be accomplished using any of the procedures described above. FIG. 7, however, shows a coil (156) with a constant diameter wire but which has been wound on a tapered mandrel. The central section (157) of the coil (156) is of generally constant diameter. The end section (158) portrayed has a decreasing diameter as the end of the coil is approached.

Clearly, it is our intent that the flexibility of the various sections of our inventive coil need not be a constant, but may vary along the axis. The variation may be linear or may vary at some other rate.

Figure 8A:
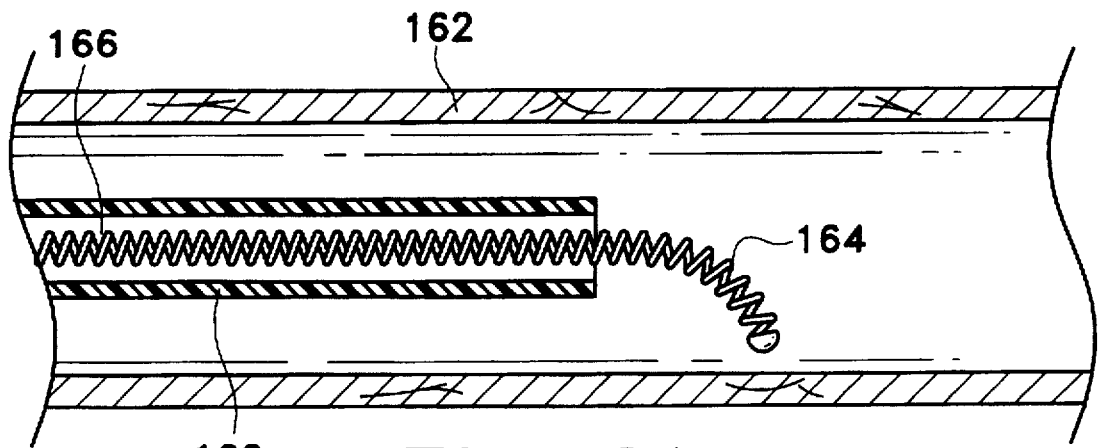
FIGS. 8A, 8B, and 8C show the procedure for deploying a vaso-occlusive made according to the invention and depict the way in which the device reacts as it deployed into a vascular lumen.
Figure 8B:
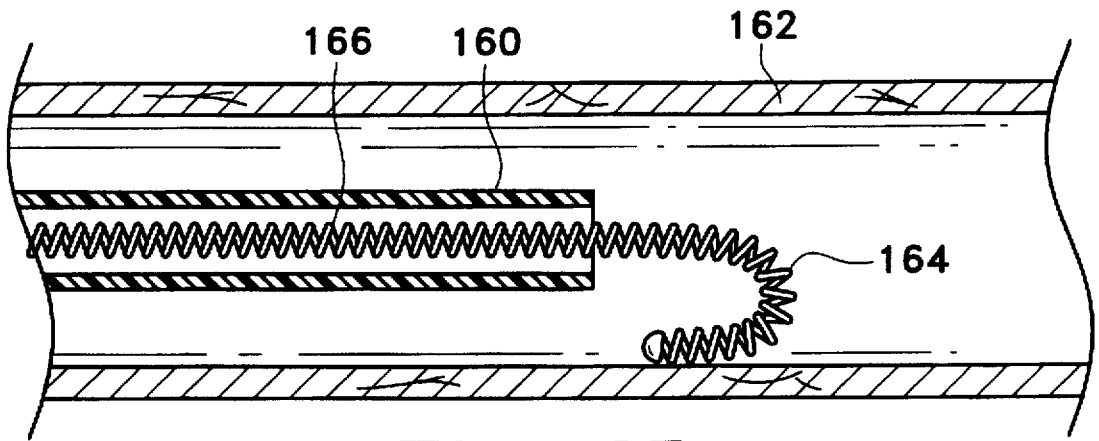
Figure 8C:
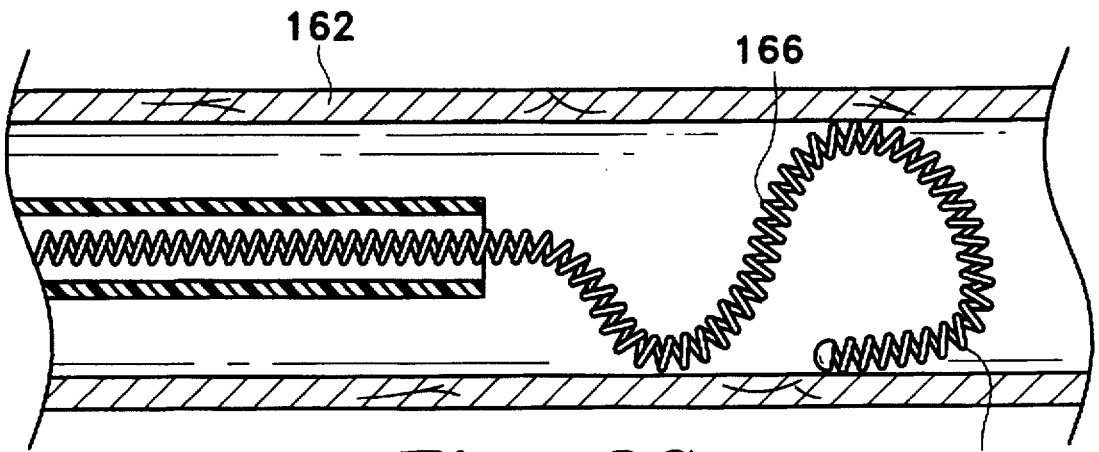

FIGS. 8A, 8B, and 8C depict a common deployment method for the inventive vaso-occlusive devices described here. It may be observed that these procedures are not significantly different than those described in the Ritchart et al. patent mentioned above. The major difference in the procedure is the ability of the end section of vaso-occlusive to quickly bend as it exits the catheter and engage the lumen wall. Specifically, FIG. 8A shows the distal tip of a catheter (160) which is within the lumen of an artery (162). The distal or end section (164) of the vaso-occlusive device is shown emanating from the distal tip of catheter (160). The beginning of, or distal of the mid-section (166) of the vaso-occlusive device is shown proximally of the lumen. In FIG. 8A, the distal end portion (164) vaso-occlusive device is beginning to "droop" toward the wall of the blood vessel (162).

In FIG. 8B, the end section (164) of the vaso-occlusive device has proceeded farther out of the catheter (166) and has engaged the wall of the blood vessel (162). In FIG. 8C, the end section (164) is completely along the wall of vessel of (162) and the secondary shape of the vaso-occlusive device is beginning to form. The mid-section (166) extends from one vascular wall to the other. As the vaso-occlusive device continues to extend from the catheter, it will become more convoluted and will form an occlusive site within vessel (162).

Modification of the above-described variations of carrying out the invention that would be apparent to those of skill in the fields of medical device design generally, and vaso-occlusive devices specifically, are intended to be within the scope of the following claims.

We claim as our invention:

1. A vaso-occlusive device for delivery into a vasculature within a constraining tubular member having an internal lumen comprising:

an elongated wire wound into a single-helix tubular member having a first end, a second end, an axis extending between said first end and said second end, and a central region between said first end and said second end, wherein the tubular member has a first configuration conforming to said constraining tubular member inner lumen when constrained within said constraining tubular member, and wherein the tubular member has a second self-forming secondary configuration, different from the first configuration, when not constrained by the constraining tubular member, and wherein the tubular member measured generally perpendicular to the axis at at least one of the first end and second end and measured in said first configuration is more flexible than is the tubular member in the central region.

2. The vaso-occlusive device of claim 1 wherein the elongated wire in the more flexible of said at least one of the first end and second end is more flexible than is the elongated wire in the central region.

3. The vaso-occlusive device of claim 2 wherein the elongated wire has a smaller diameter in said more flexible at least one of the first end and second end.

4. The vaso-occlusive device of claim 2 wherein the elongated wire in said more flexible at least one of the first and second end comprises a material which is inherently more flexible than is the elongated wire comprising the central region.

5. The vaso-occlusive device of claim 4 wherein the elongated wire in said more flexible at least one of the first end and second end has been annealed to soften the elongated wire.

6. The vaso-occlusive device of claim 1 wherein the tubular member primary configuration has a helical pitch spacing and said helical pitch spacing in the more flexible at least one of the first end and second end is longer than the pitch spacing in the central region.

7. The vaso-occlusive device of claim 1 wherein the tubular member has a first diameter in the central region and a relatively smaller second diameter in the more flexible at least one of the first end and second end.

8. The vaso-occlusive device of claim 1 wherein the tubular member has a first diameter in the central region and a relatively smaller, decreasing second diameter in the more flexible at least one of the first end and second end.

9. The vaso-occlusive device of claim 1 additionally comprising a cap on at least one of the first end and second end.

10. The vaso-occlusive device of claim 1 additionally comprising filamentary material attached to said tubular member.

11. The vaso-occlusive device of claim 1 additionally comprising a deployment tip attached to at least one of the first end and second end.

12. The vaso-occlusive device of claim 11 wherein the deployment tip comprises a mechanically detachable end adapted to attach to and detach from a pusher.

13. The vaso-occlusive device of claim 11 wherein the deployment tip comprises an electrolytically detachable end adapted to detach from a pusher by imposition of a current on said pusher.

14. The vaso-occlusive device of claim 1 wherein both the first and the second end are more flexible than is the central region.

* * * * *